United States Patent [19]

Hennessy

[11] 4,288,316
[45] Sep. 8, 1981

[54] FECAL EXAMINING DEVICE

[76] Inventor: Michael J. Hennessy, 1673 E. Oak Rd., Vineland, N.J. 08360

[21] Appl. No.: 123,370

[22] Filed: Feb. 21, 1980

[51] Int. Cl.³ ............................................... B03B 7/00
[52] U.S. Cl. ..................................... 209/17; 209/173; 422/101
[58] Field of Search ..................... 209/3, 17, 173, 250, 209/268, 273; 356/36; 422/101, 102; 23/230 B; 73/425, 425.2

[56] References Cited

U.S. PATENT DOCUMENTS

| 3,819,045 | 6/1974 | Greenwald | 209/17 |
| 3,936,373 | 2/1976 | Studer | 209/17 |
| 4,225,423 | 9/1980 | Cotey | 209/17 X |

Primary Examiner—Ralph J. Hill
Attorney, Agent, or Firm—Thomas A. Lennox

[57] ABSTRACT

A fecal examining device for use in the float separation of parasite eggs from feces with a screen composed of slots having an effective flow area of at least 40% of the surface area interposed in the liquid to allow ova to pass through the screen to a collecting slide.

14 Claims, 5 Drawing Figures

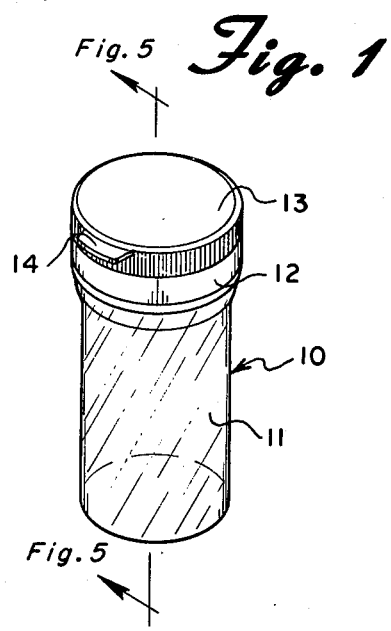
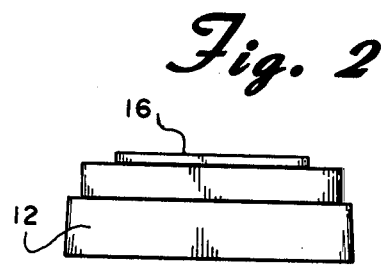
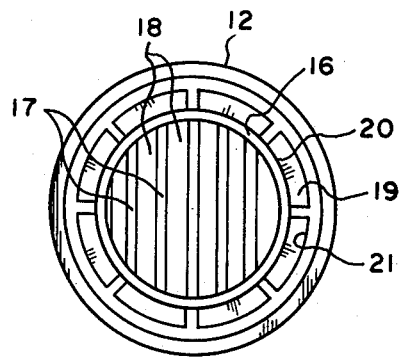
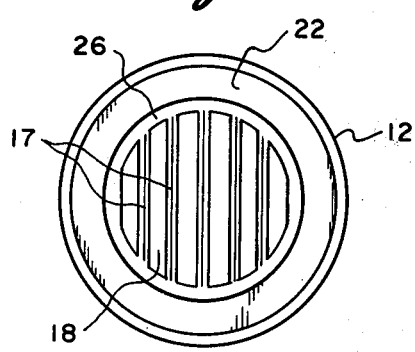
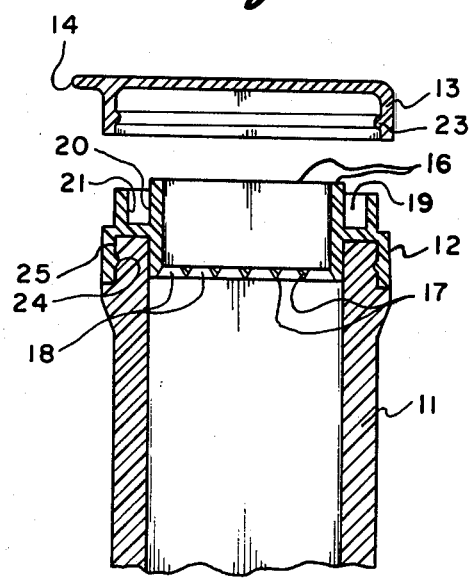

FECAL EXAMINING DEVICE

BACKGROUND OF THE INVENTION

Most animals, even the domesticated ones, and many people harbor intestinal parasites which are sometimes detrimental to health and well being. Many of these intestinal parasites produce microscopic eggs or ova which become mixed with feces. The discovery and identification of worm ova in feces is essential to the diagnosis of certain parasite infestations in man and animals. The examination of feces is commonly and frequently performed in most medical laboratories and in veterinary hospitals.

There are a number of methods and techniques of discovery and identifying parasite eggs in feces. These methods have gradually evolved from the direct examination of a fecal smear on a microscope slide. Concentration techniques using centrifugation or floatation increased test efficiency and improved the accuracy of the determination.

A prior method is to mix a bit of feces and a drop of water on microscope slide to be examined at 100 power magnification. While this method is rapid and easily completed, eggs and oocysts are not concentrated. The number of eggs is small and if the technician is not extremely conscientious, the diagnosis may easily be missed.

A concentration technique includes thoroughly mixing the feces with a flotation liquid, such as sugar water, by stirring with a wooden applicator stick. The higher specific gravity of the fluid causes the eggs to float to the surface where they can be collected on a microscope slide. As the eggs float to the surface to reach the slide on the surface of the liquid, they can be harvested for examination with the microscope. Debris such as grass and other roughage obstruct the eggs from reaching the surface and impedence to ova recovery seriously effects test efficiency and accuracy. This concern is significant with animals eating a substantial amount of roughage. Early efforts to remove extraneous matter and clumps of feces from the flotation solution including pouring the mixture through cheese cloth or wire mesh. This system was unpleasant and posed potential contamination of the premises as well as the operator.

More recently, Robert J. Greenwald in U.S. Pat. No. 3,819,045 described a fecal analyzer utilizing a perforated plate equipped with a plunger which is inserted in a cup containing the fecal/liquid suspension. The perforated plate is equipped with holes of a diameter in the range of "well above 0.5 millimeter" and "well below 1.5 millimeter" while indicating that holes of 1 millimeter are particularly suitable. The use of the Greenwald apparatus is an improvement over the straining method, but still requires substantial handling by the operator. As the strainer is pushed into the mixing chamber, debris is forced to the bottom of the container but splash back is frequent and contamination is a common occurance. This device has been marketed under the trademark "FECALYZER" by EVSCO Pharmaceutical Corp.

In U.S. Pat. No. 3,936,373, A. D. Studer describes another device directed to the test. In this device a filter thimble is inserted into the cup containing the fecal/fluid mixture. Holes in the range of 1.0 to 1.5 millimeter are provided in the thimble with the holes spaced apart about 1.5 millimeter. This provides for about 20% flow-through area if the surface were at right angles to the flow direction. The vast majority of the holes are in the vertical wall of the timble thus severely reducing the flow area through which the ova must pass to reach the surface of the liquid and the microscope slide. A device similar to that described in the Studer Patent is marketed under the trademark "OVASSAY" by Pitman-Moore, Inc. utilizing a cone-shaped strainer with essentially horizontal apertures over the entire sloped surface of the cone. This commercial device provides essentially no vertical passageways through which the ova can easily pass.

Control tests using these devices indicate that the screen systems can prevent fifty to seventy-five percent or even all of the ova from reaching the microscope slide, that would otherwise have reached the surface. For some "hard to test" ova the screens can prevent all of the ova from reaching the screen, particularly for shorter test periods. Although these devices have allegedly reduced the interference and impedence by fecal matter, the imposition of a screen appear to impede the flow of the ova to an even greater degree.

In order to satisfy the above limitations, the following objects and aims are provided:

It is an object of my invention to provide a fecal analyzer with increased test efficiency and improved accuracy.

It is a further object of this invention to provide a fecal analyzer that requires minimal handling of the feces and the liquid suspension of the feces and allows the operator to collect the ova without significant contamination of either the laboratory or the operator.

It is a particular object of this invention to provide a fecal analyzer that is particularly effective for domesticated pets and humans and those animals that do not consume a substantial amount of grass or other roughage and yet provide a separation barrier between the feces and the ova collection point.

It is a particular object of this invention to provide a separation device that will prevent large clumps of feces from reaching the ova collection point but that will basically allow the ova to rise essentially unimpeded through the screen device.

It is a further object of this invention to provide a method of handling a feces sample and collection of the ova possibly intrained in the feces without any significant chance of contamination of either the premises or the operator by material carried in the feces matter.

These and other objects, while not satisfied by the above prior art, will become apparent through the reading of the balance of the specification.

SUMMARY OF THE INVENTION

To satisfy the above objectives, I have developed a fecal examining device for collection of ova on a microscope slide whereby the slide receives and collects ova floating upward through a flotation fluid from the fecal material. A vial for holding a sample of feces to be examined is fitted with a tubular extension sealably fitted to the upper edge of the vial with an upper edge of the extension arranged to receive the microscope slide. A screen means is affixed across the tubular extension preferably near the bottom of the tubular extension. Wherein the screen means provides an essentially vertical flow area of at least 40 percent of the screen area. The tubular extension is preferably connected to the vial by a snap fit means to seal against leakage when the fluid mixture in the vial extension combination is filled to the point where the slide receives and collects the ova.

It is preferred that the screen apertures be slots having a width of 1.5 to 2.5 millimeters and that the overall area of the slots to be in the range of 40 percent to 95 percent of the screen area. It is more preferred that the vertical cross-sectional area of the apertures be in the range of 55 percent to 85 percent of the screen, more preferably be in the range of 65 percent to 75 percent of the screen area, and most preferably about 70 percent.

It is preferred that a circumferential trough be provided around the area for receiving the collection slide such that when the slide is placed on the liquid meniscus the overflow fluid is caught in the trough. A cover capable of fitting over either the vial or over the exposed end of the tubular extension is preferably provided for transportation, storage or discard of the entire unit.

I have discovered that utilization of the above device provides a multifold improvement in performance, that the screen provides a sufficient barrier for the operator and that the substantial improvement in diagnosis is a great aid to the diagnostician for examination of feces of humans and animals that do not consume substantial quantities of roughage.

BRIEF DESCRIPTION OF DRAWINGS

FIG. 1 is a perspective view of fecal examining device of this invention.

FIG. 2 is a side view of the tubular extension disattached from the vial shown in FIG. 1.

FIG. 3 is a top view of the tubular extension shown in FIG. 2.

FIG. 4 is a bottom view of the tubular extension shown in FIG. 2.

FIG. 5 is a cross-sectional view taken along line 5-5 of FIG. 1 to show the detail of the tubular extension.

DESCRIPTION OF PREFERRED EMBODIMENTS

In FIG. 1 the fecal examining device 10 is shown in a perspective view with all parts interfitted together for use, storage or disposal. Vial 11 is an injection molded clear plastic vial having a capacity of about 20 cc. with an outside diameter of about 30 millimeters. Vial 11 may be colored, tinted, translucent or opaque. Tubular extension 12 is snap-fitted and sealably connected to vial 11. Cap 13 snap fits on the top of tubular extension 12 or before the tubular extension is in place it will sealably cover vial 11. Thumb lip 14 allows cap 13 to be removed by forcing the lip upwards to remove ductile cap 13. On upper edge 16 of tubular extension 12 is placed a microscope slide on which the ova collect for later microscope examination. Looking from the top in FIG. 3, upper edge 16 surrounds the tubular cavity which terminates in screen 26 through which slotted apertures 18 allow the ova to pass through upwardly to the slide resting on upper edge 16. Slots 18 are each two millimeters wide each separated by rail guards 17, about 1 millimeter wide. Slots 18 range from about one-half inch to about three-quarters inch in length. Annular trough 19 is formed between wall 20 and the inside of outside wall 21 for overflow at upper edge 16. Looking from below in FIG. 4, the bottom of screen 26 is shown together with slotted apertures 18. Annular groove 22 is provided to fit over and sealably snap onto the upper edge of vial 11. In FIG. 5 the cross-section shows how each part of device 10 fits together but with cap 13 exploded off to better show the upper configuration tubular extension 12. As now can be observed, annular ridge 23 snap fits over tubular extension 12 to seal cap 13 against upper edge 16. Likewise annular shelf 24 snaps into annular groove 22 to hold tubular extension 12 firmly and sealably over rim 25 on the top of vial 11 to sealably close and prevent leakage between the two components.

Ribs 28 reinforce the structure between inner wall 20, which extends to the highest elevation to receive the microscope slide, and wall 21 which together form trough 19. In this embodiment, the aperture area through screen 17 is provided to allow ova to pass essentially unimpeded through slots 18 past rail guards 26, with an effective vertical flow area of almost 60 percent.

In the preferred embodiments the harvesting chamber being the interior of tubular extension 12, is protected against intrusion of fecal clumps by parallel rail guards preferably 4 to 7 in number near the bottom of the havesting chamber. The rails are preferably about 1 millimeter wide and have round, square or triangular cross-section, although the prisim shape of rails 26 with an edge point downwardly and a face horizontal on the top is preferred. The rails are molded as part of the tubular extension 12 from stereoregular polypropylene, polyethylene, polyvinyl chloride, or like materials with sufficient ductility to sealably fit over vial 11, preferably constructed of a semirigid plastic such as acrylonitrile-styrene copolymer, or like material. The interconnection between tubular extension 12 and and vial 11 may be the snap fit shown above or may be constructed to interfit and actually interlock upon twisting to prevent inadvertent disengagement. Actually, it is preferred that the fecal examining device be constructed of materials and in a fashion to be discarded after use. Thus, when the fecal matter is placed in vial 11 and a fluid suspension created by mixing with a wooden paddle or like instrument, the top of vial 11 will be open. After sufficient fecal matter has gone into suspension in the fluid, tubular extension 12 is snapped into place and thereafter need not be removed. It is not necessary to suspend all of the fecal matter as rail guards 26 will prevent any clumps lighter than the fluid from reaching the harvesting chamber in tubular extension 12. After extension 12 has been sealably interfitted on vial 11, additional fluid is poured into vial 11 through extension 12 filling not only the balance of the vial but the tubular extension so that the fluid forms a meniscus at upper edge 16. A microscope slide is placed on edge 16 and after the eggs have been harvested, lid 13 is snapped on depressions 15 to seal the cap on upper edge 16 for storage and subsequent disposal.

The size and position of upper edge 16 forms a cradle for a microscope slide to be placed on the liquid so that ova rising in the fluid will reach and attach to the slide so that when the slide is removed after a period of about fifteen to thirty minutes, the ova, if present, will have been effectively harvested for observation and diagnosis.

The following procedures are supplied to demonstrate the utility and effectiveness of my invention:

Ova infested canine and feline fecal samples are collected from canine, feline and human animals on a standard low residue type diet. The samples are handled using the above method with a succrose-phenol solution of a 1.2 to 1.3 specific gravity and allowed fifteen minutes to collect the ova. The samples are coded with sample numbers 1 through 5, one for each animal. The code designations for possible worm infestation are "H" for hookworm; "W" for whipworm and "R" for roundworm. The test results for tapeworm and coccidia are negative and are not included.

Each sample is tested using three devices using the method described above as follows:

Device A: The device of this invention shown in FIGS. 1 through 5.

Device B: The commercially available Greenwald device as described in U.S. Pat. No. 3,819,045 referred to hereinabove.

Device C: An "OVASSAY" device marketed by Pitman Moore, Inc., Washington Crossing, New Jersey, similar to that described in U.S. Pat. No. 3,936,373 referred to hereinabove, except that the shape of the thimble is cone shaped and with square horizontal apertures extending over the slanted surface.

The following results in Table I represent the number of eggs observable under 100 power magnification with each device.

TABLE I

| Ova Type | Sample Designation | | | | |
|---|---|---|---|---|---|
|  | 1 | 2 | 3 | 4 | 5 |
| *Device A* | | | | | |
| Hook | 168 | 205 | 0 | 0 | 321 |
| Whip | 4 | 5 | 0 | 3 | 8 |
| Round | 208 | 0 | 132 | 18 | 0 |
| *Device B* | | | | | |
| Hook | 48 | 87 | 0 | 0 | 115 |
| Whip | 1 | 1 | 0 | 0 | 2 |
| Round | 192 | 0 | 20 | 5 | 0 |
| *Device C* | | | | | |
| Hook | 60 | 73 | 0 | 0 | 94 |
| Whip | 1 | 0 | 0 | 0 | 3 |
| Round | 204 | 0 | 44 | 5 | 0 |

Throughout this specification the term "screen area" is used with reference to the vertical flow area available for ova flow to the collection slide. By this term it is intended to mean the internal cross-sectional area taken by a horizontal plane across the tubular extension. Thus for example, the vertical flow area could be calculated by determining the inside cross-sectional area of the cylindrical extension and subtracting the area impeded by the rails. That lesser area divided by the inside area yields a measure of vertical flow area. Extension 12 has a vertical flow area of about 70 percent. Of course, the tubular extension may have any shape cross-section, but is preferably cylindrical.

The prior examples of my invention are merely illustrative of my invention and are not intended to limit the scope of a patent grant. My invention is limited only by the appended claims:

I claim:

1. A fecal examining device to support an ova-collecting slide whereby the slide receives and collects ova upwards through a liquid-fecal material mixture comprising:
   (a) a vial for holding a sample of feces to be examined,
   (b) a tubular extension with an upper edge of the extension constructed to receive the ova-collecting slide wherein a lower portion of the tubular extension is connected to the vial opening by a sealable fit means to sealably connect the parts and expand the internal volume of the device upwardly to the extent of the internal volume of the tubular extension, and
   (c) a screen means immovably affixed across the internal volume of the tubular extension wherein the screen means comprises a plurality of said guards providing an essentially clear vertical flow area upwardly of at least 40% of the screen area.

2. The fecal examining device of claim 1 wherein the vial is a clear plastic cup capable of standing on its own.

3. The fecal examining device of claim 1 wherein the area for vertical flow of the ova through the screen is the range of 40 percent to 95 percent of the screen area.

4. The fecal examining device of claim 1 wherein the area for vertical flow of the ova through the screen is the range of 55 percent to 85 percent of the screen area.

5. The fecal examining device of claim 1 wherein the area for vertical flow of the ova through the screen is the range of 65 percent to 75 percent.

6. The fecal examining device of claim 1 wherein the screen is constructed to have a plurality of adjacent parallel slots between the rail guards to allow the ova to pass through the screen and to the collection surface.

7. The fecal examining device of claim 6 wherein the screen is at least two rail guards extending horizontally across the internal volume of the tubular extension with at least 40 percent vertical flow area.

8. The fecal examining device of claim 6 wherein the screen is at least four rail guards extending horizontally across the internal volume of the tubular extension with at least 55 percent to 85 percent vertical flow area.

9. The fecal examining device of claim 6 wherein the rail guards have a triangular cross-section with one edge of the rail guard pointed downwardly.

10. The fecal examining device of claim 1 wherein an annular trough is provided outside the upper edge of the tubular extension on which the ova collecting slide is placed, to catch the overflow fluid.

11. The fecal examining device of claim 1 wherein a cover is provided to seal either the vial alone or the upper edge of the tubular extension.

12. A method for collecting ova using a fecal examining device comprising:
   (a) placing the fecal sample in the vial for holding a sample of feces to be examined,
   (b) adding to the vial fluid of a specific gravity greater than that of the ova to be collected,
   (c) mixing the feces into a suspension in the fluid,
   (d) snapping a tubular extension onto the top of the vial wherein the tubular extension is equipped with an upper edge of the extension constructed to receiving the ova-collecting slide, wherein a lower portion of the tubular extension is snapped to the vial opening by a sealable fit means to sealably connect the parts and expand the internal volume of the device upwardly to the extent of the internal volume of the tubular extension, wherein a screen means is immovably affixed across the internal volume of the tubular extension, and wherein the screen means comprises a plurality of rail guard providing an essentially clear vertical flow area upwardly of at least 40% of the screen area,
   (e) adding sufficient fluid through the top of the tubular extension to the suspension to bring the liquid level up to a meniscus at the top of the tubular extension,
   (f) placing a collecting slide over the meniscus and allowing the ova, if any, to collect on the under side of the microscope slide, and (g) removing the slide and examining the under surface of the slide under a microscope for the presence of ova.

13. A fecal examining device to support an ova-collecting slide whereby the slide receives and collects ova upwards through a liquid-fecal material mixture comprising:
   (a) a vial capable of standing on its own with its opening upwardly for holding a sample of feces to be examined,
   (b) a tubular extension with an upper edge of the extension constructed to receive the ova-collecting slide wherein a lower portion of the tubular extension is connected to the via opening by a snap sealing fit means to sealably connect the parts and expand the internal volume of the device upwardly to the extent of the internal volume of the tubular extension, and
   (c) a screen means affixed horizontally across the internal volume of the tubular extension near the bottom of the extension, wherein the screen means is at least one horizontal rail guard having a triangular cross-section with one edge directed downwardly and provides an essentially clear vertical flow area upwardly of at least 40 percent of the area.

14. The fecal examining device of claim 13 wherein the screen means comprises five horizontal rail guards with a vertical flow area of about 60 percent.

* * * * *